(12) United States Patent
Horn et al.

(10) Patent No.: US 7,885,446 B2
(45) Date of Patent: Feb. 8, 2011

(54) SYSTEM AND METHOD TO DETECT A TRANSITION IN AN IMAGE STREAM

(75) Inventors: Eli Horn, Kiryat Motzkin (IL); Hagai Krupnik, Nofit (IL); Ofra Zinaty, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 0 days.

(21) Appl. No.: 12/719,601

(22) Filed: Mar. 8, 2010

(65) Prior Publication Data
US 2010/0166272 A1 Jul. 1, 2010

Related U.S. Application Data

(63) Continuation of application No. 11/235,541, filed on Sep. 27, 2005, now Pat. No. 7,684,599.

(60) Provisional application No. 60/612,792, filed on Sep. 27, 2004.

(51) Int. Cl.
*G06K 9/00* (2006.01)

(52) U.S. Cl. .............. 382/128; 382/199; 382/173; 348/65; 600/109; 600/117

(58) Field of Classification Search ........... 382/128
See application file for complete search history.

(56) References Cited

U.S. PATENT DOCUMENTS

| | | | |
|---|---|---|---|
| 4,854,328 A | 8/1989 | Pollack | |
| 5,209,220 A * | 5/1993 | Hiyama et al. ............ 600/109 |
| 5,331,551 A * | 7/1994 | Tsuruoka et al. .......... 382/128 |
| 5,572,252 A | 11/1996 | Naka et al. | |
| 5,596,366 A | 1/1997 | Takashima et al. | |
| 5,604,531 A | 2/1997 | Iddan et al. | |
| 5,647,368 A * | 7/1997 | Zeng et al. ................ 600/476 |
| 5,649,021 A * | 7/1997 | Matey et al. .............. 382/128 |
| 5,738,110 A | 4/1998 | Beal et al. | |
| 5,833,603 A | 11/1998 | Kovacs et al. | |
| 5,873,830 A | 2/1999 | Hossack et al. | |

(Continued)

FOREIGN PATENT DOCUMENTS

GB    2 374 149    10/2002

(Continued)

OTHER PUBLICATIONS

Medscape Gastroenterology, "A Mosaic Pattern of the Descending Duodenum", Medscape Gastroenterology, vol. 2, No. 1, Medscape, <URL:http://www.medscape.com/viewarticle/405488_2>, retrieved Jun. 2, 2008.

(Continued)

*Primary Examiner*—Sath V Perungavoor
(74) *Attorney, Agent, or Firm*—Pearl Cohen Zedek Latzer, LLP

(57) ABSTRACT

A system and method may detect a transition in an image stream captured within a body lumen. One or more parameters may be computed at points corresponding to a time scale of the image stream. Transition in the values of the parameters may be identified and may indicate a location along the body lumen. The image stream may be segmented at the transition points identified.

19 Claims, 4 Drawing Sheets

U.S. PATENT DOCUMENTS

| | | | |
|---|---|---|---|
| 6,053,873 | A | 4/2000 | Govari et al. |
| 6,402,689 | B1 | 6/2002 | Scarantino et al. |
| 6,428,469 | B1 | 8/2002 | Iddan et al. |
| 6,635,834 | B1 | 10/2003 | Wenner |
| 6,709,387 | B1 | 3/2004 | Glukhovsky et al. |
| 6,900,790 | B1 | 5/2005 | Doi et al. |
| 6,947,788 | B2 | 9/2005 | Gilboa et al. |
| 6,950,690 | B1 * | 9/2005 | Meron et al. ............... 600/424 |
| 7,022,067 | B2 * | 4/2006 | Glukhovsky et al. ........ 600/109 |
| 7,136,518 | B2 * | 11/2006 | Griffin et al. ............... 382/133 |
| 7,190,818 | B2 * | 3/2007 | Ellis et al. .................. 382/128 |
| 7,221,388 | B2 * | 5/2007 | Sudo et al. .................... 348/71 |
| 7,228,166 | B1 | 6/2007 | Kawasaki et al. |
| 7,232,410 | B2 * | 6/2007 | Takahashi .................. 600/180 |
| 7,295,226 | B1 | 11/2007 | Meron et al. |
| 7,316,647 | B2 | 1/2008 | Kimoto et al. |
| 7,319,781 | B2 | 1/2008 | Chen et al. |
| 7,684,599 | B2 * | 3/2010 | Horn et al. ................. 382/128 |
| 2001/0051766 | A1 | 12/2001 | Gazdzinski |
| 2002/0042562 | A1 | 4/2002 | Meron et al. |
| 2002/0103425 | A1 | 8/2002 | Mault |
| 2002/0173718 | A1 | 11/2002 | Frisch et al. |
| 2002/0198439 | A1 * | 12/2002 | Mizuno ....................... 600/109 |
| 2003/0016864 | A1 * | 1/2003 | McGee et al. ............... 382/165 |
| 2003/0020810 | A1 * | 1/2003 | Takizawa et al. .............. 348/68 |
| 2003/0077223 | A1 * | 4/2003 | Glukhovsky et al. ......... 424/9.1 |
| 2003/0142753 | A1 * | 7/2003 | Gunday ................. 375/240.29 |
| 2004/0073087 | A1 | 4/2004 | Glukhovsky et al. |
| 2004/0111011 | A1 | 6/2004 | Uchiyama et al. |
| 2004/0115877 | A1 | 6/2004 | Iddan |
| 2004/0180391 | A1 | 9/2004 | Gratzl et al. |
| 2004/0225223 | A1 * | 11/2004 | Honda et al. ................ 600/476 |
| 2004/0249291 | A1 * | 12/2004 | Honda et al. ................ 600/476 |
| 2005/0074151 | A1 * | 4/2005 | Chen et al. ................. 382/128 |
| 2005/0075537 | A1 * | 4/2005 | Chen et al. ................. 600/109 |
| 2005/0075551 | A1 * | 4/2005 | Horn et al. .................. 600/361 |
| 2005/0148816 | A1 | 7/2005 | Glukhovsky et al. |
| 2005/0171418 | A1 | 8/2005 | Lin |
| 2005/0196023 | A1 * | 9/2005 | Chen et al. ................. 382/128 |
| 2005/0215876 | A1 * | 9/2005 | Chen et al. ................. 600/407 |
| 2005/0228293 | A1 * | 10/2005 | Cahill et al. ............... 600/478 |
| 2005/0288594 | A1 | 12/2005 | Lewkowicz et al. |
| 2006/0050966 | A1 * | 3/2006 | Nishimura et al. .......... 382/209 |
| 2006/0069317 | A1 * | 3/2006 | Horn et al. .................. 600/300 |
| 2006/0155174 | A1 | 7/2006 | Glukhovsky et al. |
| 2006/0164511 | A1 | 7/2006 | Krupnik |
| 2006/0193505 | A1 | 8/2006 | Glukhovsky et al. |
| 2006/0217593 | A1 | 9/2006 | Gilad et al. |
| 2006/0239557 | A1 * | 10/2006 | Cahill et al. ................. 382/181 |
| 2007/0053557 | A1 * | 3/2007 | Cahill et al. ................. 382/128 |
| 2007/0135715 | A1 * | 6/2007 | Inoue et al. ................. 600/477 |
| 2007/0165924 | A1 * | 7/2007 | Nicponski ................... 382/128 |
| 2007/0165932 | A1 * | 7/2007 | Nishimura et al. .......... 382/128 |
| 2007/0165942 | A1 * | 7/2007 | Jin et al. ..................... 382/154 |
| 2007/0292011 | A1 * | 12/2007 | Nishimura et al. .......... 382/128 |
| 2009/0196476 | A1 * | 8/2009 | Inoue .......................... 382/128 |

FOREIGN PATENT DOCUMENTS

| | | |
|---|---|---|
| WO | WO 99/30610 | 6/1999 |
| WO | WO 02/082979 | 10/2002 |

OTHER PUBLICATIONS

Office Action for U.S. Appl. No. 11/235,541 mailed on Sep. 8, 2008.

Berens et al., "Stomach, Intestine and Colon Tissue Discriminators for Wireless Capsule Endoscopy Images", Proc of SPIE, vol. 5747, pp. 283-290, 2005.

Final Office Action for U.S. Appl. No. 11/235,541 mailed on Feb. 25, 2009.

Notice of Allowance for U.S. Appl. No. 11/235,541 mailed on Aug. 21, 2009.

Office Action for U.S. Appl. No. 10/493,751 mailed on Apr. 20, 2007.

Office Action for U.S. Appl. No. 10/493,751 mailed on Oct. 18, 2007.

Office Action for U.S. Appl. No. 10/493,751 mailed on Mar. 26, 2008.

Office Action for U.S. Appl. No. 10/493,751 mailed on Mar. 18, 2009.

Office Action for U.S. Appl. No. 10/493,751 mailed on Aug. 13, 2009.

International Search Report for International Application No. PCT/IL03/01080 mailed on Aug. 23, 2004.

European Office Action for European Application No. 03 77 8736 mailed on May 12, 2009.

Supplementary European Search Report for European Application No. EP 03 77 8736 completed Apr. 7, 2008.

* cited by examiner

SYSTEM AND METHOD TO DETECT A TRANSITION IN AN IMAGE STREAM

CROSS-REFERENCE TO RELATED APPLICATIONS

This application is a continuation of U.S. application Ser. No. 11/235,541 filed Sep. 27, 2005, now U.S. Pat. No. 7,684,599 entitled "System and Method to Detect a Transition in an Image Stream", and claims the benefit of U.S. Provisional Application No. 60/612,792 filed Sep. 27, 2004, entitled "System and Method to Indicate In-Vivo Location", both of which are incorporated by reference herein in their entireties.

FIELD OF THE INVENTION

The present invention relates to in-vivo imaging and more specifically to a system and method for detecting a transition in an image stream, typically based on at least image processing.

BACKGROUND OF THE INVENTION

Devices are known to provide in-vivo imaging, diagnosis, treatments etc. For example, autonomous in-vivo devices, such as swallowable capsules, may move through a body lumen, collecting data, for example image data, as they move along. This data may be transmitted to an external reception device, and processed by a processing unit, for example, to help determine in-vivo parameters. Typically, image data collected from within a body lumen, such as the gastrointestinal (GI) tract, may be transmitted to an external receiving unit and may be displayed as a moving image stream on a monitor outside a patient's body. The images may be combined in sequence, and a moving image of, for example, more then 120 minutes in length, may be presented to a user. It may be advantageous to provide a user, such as a physician, with tools for shortening the viewing or diagnosis time of such a movie without compromising the information presented in the movie.

SUMMARY OF THE INVENTION

Embodiments of the present invention provide a system and method for indicating in-vivo location, for example by indicating transition in one or more parameters sampled along a body lumen and/or within a body lumen. Viewing may be assisted by indicating in-vivo location in a captured image stream.

According to some embodiments a system is provided which includes an in-vivo imaging device, such as an autonomous, typically swallowable imaging capsule; an external receiving unit for receiving image data from the in-vivo imaging device; and a processor for determining an in-vivo location of received images. According to some embodiments the received images may be displayed to a user, for example, as a moving image stream, and the in-vivo location of images within the stream may be indicated to the user. According to some embodiments the processor may utilize image processing based on parameters such as pixel, spatial-spectral characteristics, shape, and/or other parameters. According to further embodiments in-vivo device localization techniques, for example, as known in the art, may be used together with image processing according to embodiments of the invention, to give indication of in-vivo location.

Embodiments of the invention also provide a method for indicating in-vivo location and/or for indicating passage from one in-vivo area to another in-vivo area. According to some embodiments, color and/or spatial-spectral characteristics and/or shape parameters, typically of in-vivo images may be used to determine in-vivo location and/or transition from one in-vivo location to another. In other embodiments, sensor output in addition to image sensor output may be used to determine an in-vivo location and/or transition.

Indication of an in-vivo location or an indication of transition from one location (e.g., the stomach) to another location (e.g., the small intestine) may provide a tool for a user to advancing the image streaming to an area of interest and cut down viewing time of an in-vivo image stream (e.g. a stream of images transmitted from the GI tract) and/or diagnosis time. For example, a user may more easily find a specific in-vivo location of interest rather than have to watch the entire movie to review images from the specific location.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein.

Figure 1:
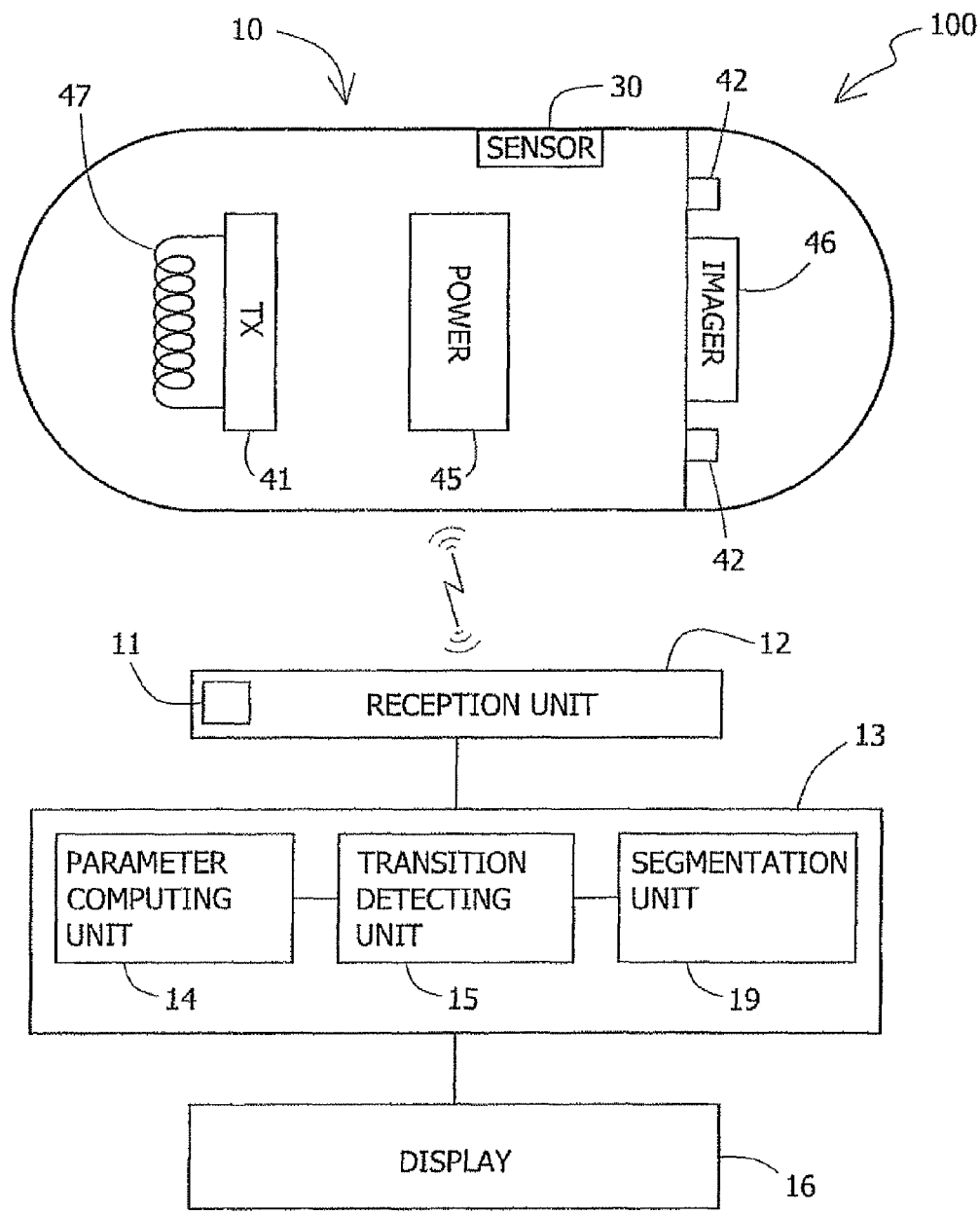
FIG. 1 is a schematic illustration of an in-vivo system according to one embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements throughout the serial views.

DETAILED DESCRIPTION OF THE INVENTION

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the following detailed description, numerous specific details are set forth in order to provide a thorough understanding of the present invention. However, it will be understood by those skilled in the art that the present invention may be practiced without these specific details. In other instances, well-known methods, procedures, and components have not been described in detail so as not to obscure the present invention.

Some embodiments of the present invention are directed to a typically swallowable in-vivo device that may be used for gathering and/or capturing in-vivo data, for example from the entire and/or part of a length of the gastrointestinal (GI) tract, and transmitting captured data to a receiving and/or processing unit. Other embodiments need not be swallowable or autonomous, and may have other shapes or configurations. Yet other embodiments may be used for gathering image or other data from other body lumens, such from blood vessels, from the urinary tract, from the reproductive tract etc. According to some embodiments the in-vivo device may include an image sensor however, other sensors may be used. Devices according to embodiments of the present invention may be similar to or operate in a similar way to embodiments described in US Patent Application Publication Number 2001-0035902 published Nov. 1, 2001 and entitled "A Device and System for In Vivo Imaging" and/or in U.S. Pat. No. 5,604,531 entitled "In-Vivo Video Camera System", each of which are assigned to the common assignee of the present invention and each of which are hereby incorporated by reference in their entirety. Furthermore, receiving, storage, processing, and/or display systems suitable for use with embodiments of the present invention may be similar to embodiments described in US Patent Application Publication Number 2001-0035902 and in U.S. Pat. No. 5,604,531. Of course, devices, systems, structures, functionalities, and methods as described herein may have other configurations, sets of components and processes etc.

Embodiments of the device are typically autonomous and are typically self-contained. For example, the device may be a capsule or other unit where all the components are substantially contained within a container or shell, and where the device does not require any wires or cables to, for example, receive power or transmit information. The device may communicate with an external receiving and display system to provide display of data, control, or other functions. For example, power may be provided by an internal battery or a wireless receiving system. Other embodiments may have other configurations and capabilities. For example, components may be distributed over multiple sites or units. Control information may be received from an external source.

Reference is now made to FIG. 1, which is a schematic illustration of an in-vivo imaging system 100, according to an embodiment of the invention. System 100 may include, for example, an in-vivo device 10, a data reception unit 12 processing unit 13, and a display unit 16. In-vivo device 10 may be, for example, a swallowable capsule. In-vivo device 10 may include, for example, one or more detection units or sensors, such as image sensor 46 and sensor 30 and one or more illumination units 42 for illuminating an in-vivo location, e.g. a body lumen, for imaging. An image sensor 46 may be, for example, a CMOS image sensor, a CCD image sensor or other suitable image sensors, e.g. solid state imagers, for imaging within a body lumen. Typically device 10 may include a transmitter 41 for transmitting image data to data reception unit 12. The transmitter may be wireless, for example, an RF, IR or microwave transmitter and may be in electrical communication with, for example, an antenna 47 and power source 45. According to other embodiments transmission may be wired. System 100 may further include a displaying apparatus 16, such as a monitor, to display at least in-vivo device data. According to some embodiments location indication may be presented on display 16. The system 100 may optionally include a data storage unit. For example, data reception unit 12 may receive the data from in-vivo device 10, and may thereafter transfer the data to a processing unit 13. Reception unit 12 may include, for example, a location sensor 11 as may be described herein. In other embodiments of the present invention, a location sensor may be included in device 10. Processing unit 13 may include a parameter computing unit 14, a transition detecting unit 15, and a segmentation unit 19. Parameter computing unit 14 may detect, determine, and/or process one or more pixel related parameter, structure related parameter, sensor sampled parameter, location parameter, and/or other parameter, e.g. as may be described herein. Transition detecting unit 15 may identify a transition in one or more parameters values detected with parameter computing unit 14 as may be described herein. Segmentation unit 19 may segment an image stream captured by device 10, for example segmentation unit 19 may segment the image stream into shortened image streams captured from specific organs, e.g. esophagus, stomach, small intestine, colon, rectum. Other segmentations may be performed. In one example, a sub-image stream may include a single image frame. The data captured by in-vivo device 10 and processed by processing unit 13 may be displayed on display 16. Data reception unit 12 may be separate from the processing unit 13 or combined with it. Processing unit 13 may be, for example, associated with and/or integral to a personal computer or workstation, and may include, for example, a processor memory etc. Processing unit 13 may be configured for real time processing, e.g. processing data as it is transmitted from in-vivo device 10 and/or for post processing to be viewed or otherwise displayed at a later date. The units 12, 13, and 16 of the system 100 may be integrated into a single unit, for example a stationary or portable workstation, or may be integrated into a plurality of units. In one example, processing unit 13 may be integral to device 10 or part of its functionality may be integral to device 10. Of course, other suitable components may be used. Device 10 may be an imaging device, and/or may include non-imaging capability.

Device 10 may be capsule shaped, and may be easily swallowed and passively passed through the entire GI tract, pushed along, for example, by natural peristalsis. Nonetheless, it should be appreciated that device 10 may be of any shape and size suitable for being inserted into and passing through a body lumen or cavity, such as spherical, oval, cylindrical, etc. or other suitable shapes. Furthermore, device 10 or various embodiments that may include at least some components of device 10 may be attached or affixed on to an instrument that may be inserted into body lumens and cavities, such as, for example, on an endoscope, laparoscope, stent, needle, catheter etc.

According to some embodiments of the present invention, correspondence between data gathered in-vivo and in-vivo location may be indicated by labeling data according to the specific in-vivo regions. For example in the GI, data captured may be categorized and/or segmented by data captured in the esophagus, stomach, small intestine and colon. Other suitable number or types of segmentations, categories and sub-categories may be defined and data may be segmented into other numbers and types of categories. According to one embodiment of the present invention segmentation may be achieved by providing a method for identifying transition points between the specified regions, segments, for example, transition points identified by transition in the values of one or more pre-determined parameters. The pre-determined parameters may be computed at points corresponding to a time scale of the image stream, for example, a first point in time may correspond to a first image frame of the image stream, a second point of time may correspond to a second image frame of the image stream etc. In one example, the pre-determined parameters may include structure related parameters, pixel related parameters, parameters related to data sampled from a sensor, e.g. temperature sensor, pH sensor, or location sensor, or other sensor.

Figure 2:
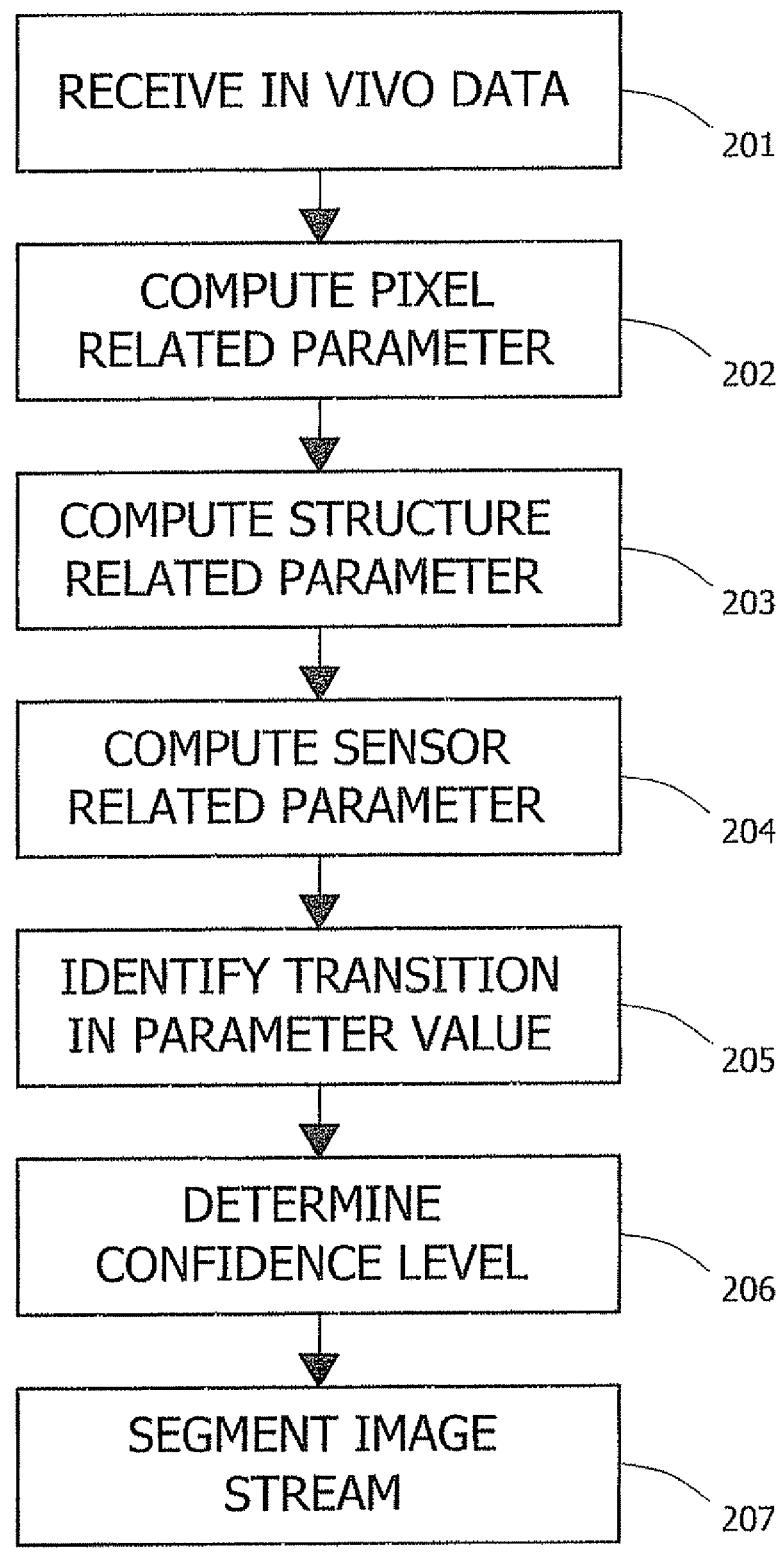
FIG. 2 is a flow depicting a method for determining a transition point between specified regions based on in-vivo data.

Reference is now made to FIG. 2, which is a flow chart depicting a method for identifying a transition point within one or more body lumens and/or a location within a body lumen according to some embodiments of the present invention. For example, a transition from one region in a body lumen to another imaged in an image stream may be identified, based on an identified change in one or more parameters measured. The parameters measured and/or computed may correspond to the time scale of the image stream. Embodiments of the method may include receiving in-vivo data, such as image data (201). In one example, an image stream including a stream of image frames of a body lumen may be received. According to one embodiment of the present invention, the image stream may image a length or portion of a body lumen, e.g. a portion of the body lumens in the GI tract. Data other than image data and/or in addition to image data may also be received, for example data sampled from sensor 30. For example, data relating to temperature, e.g. from an in-vivo temperature sensor, data related to pH, data related to speed, and/or general direction of the in-vivo device 10, or other data. Image data together with data received from other sensors may be used to determine transition from one in-vivo location, region, environment, or area to another or to determine a specific location. The data received may be used to determine an event in the data that may characterize, for example, a transition from one in-vivo location, region, environment, or area to another. For example, data other than image data and/or in addition to image data may be used to indicate in-vivo location and/or to identify transition points. Data from the image sensor and data from other sensors may be received and/or sampled at the same frequency or may be received and/or sampled at a different frequency. Transition points along the course of the GI tract may include inter alia transition between the esophagus and stomach, stomach and small intestine, and/or small intestine and colon. Other transition points or events may be identified based on in-vivo data gathered. Events, for example pathologies may be identified. Arrival to a specific location, for example, the cecum may be identified.

In one embodiment of the present invention one or more pixel related parameter may be determined and/or computed (block 202). The point, image frame, and/or corresponding time at which a change or shift in the value of one or more pixel related parameters may correspond to a specific location in the GI tract, for example, a specific transition point along the GI tract. In one example, tissue color may be known to lean more toward a reddish color in for example the stomach and lean more toward a yellowish color in the region of the small intestine. Determining, tracking or tracing the level of red and/or yellow in a stream of image frames captured along the GI tract may help identify the transition region between the stomach and small intestine. In another example, other pixel information may be traced and/or intensity level may be traced.

In yet other examples, a pattern of a parameter value, e.g. a pattern of intensity may be determined and used to identify a location in the GI tract. For example, the peristaltic contractions that may occur naturally in the GI tract may occur in different frequencies and/or with durations in different organs in the GI tract. For example, specific regions in the GI tract may have characteristic frequency patterns of contractile activity. Contractile activity may result, for example, in a change of intensity of image frames. For example the average intensity of an image frame captured while the lumen may have been closed due to a contraction, may be different than the average intensity of an image frame captured when the lumen is open. According to one embodiment of the present invention, a change in a pattern of intensity levels, or an event in the pattern of intensity levels may be used to detect transition from one region in the GI tract to another. Other identifiable patterns may be used to detect transition points. Determining contractile activity, for example, within the GI tract may be described in U.S. Patent Application No. 60/673,803 filed on Apr. 22, 2005 which is assigned to the common assignee of the present invention and which is hereby incorporated by reference in its entirety.

In another embodiment of the present invention, a structure related parameter over the course of an image stream may be computed by parameter computing unit 14 or otherwise determined (203). An identified change in one or more structure related parameter may be used to identify a location in the GI tract, for example a transition pointing the GI tract between two body lumens. For example the structure related parameter may identify the presence of villi and may be used to locate the small intestine as may be described herein. Identification of blood vessel structure may be used to identify the esophagus and/or entrance to the colon. Other structural, morphologic, or shape related parameters may be computed and/or determined and used to detect one or more locations within the GI tract and/or transition points e.g., transition from one in-vivo area to another.

In yet another embodiment, sensor related parameter, related to data sampled from a sensor other than the image sensor 46 computed (block 204) and the parameter value, for example a change in the sampled output of the sensor over time and/or the sampled output of the sensor over the time period that the image stream may have been captured may be determined, for example by parameter computing unit 14 and/or in-vivo device 10. A sensor value other than an image sensor value may also be used to detect transition from one region in the GI to another. For example in-vivo pH and/or temperature measurement may be sampled along the GI tract and used to detect a transition point. The motility, speed of advancement of device 10, acceleration along the GI tract, and/or the movement pattern of the device through the body lumen may be sampled, calculated or otherwise determined and used to detect a transition point and/or a shift in the average value of the parameter that may be characteristic of a location in the GI tract. For example, device 10 may be known to accelerate quickly through the transverse colon. Knowledge of the speed and/or acceleration of device 10 may enable detection of images or other data captured in the transverse colon. Other sensor measurements may be used, for example, location data from location sensor 11 may be used to determine a transition point.

Transition in parameter values of one or more parameters computed and the confidence may be determined (205) by for example, transition detecting unit 15. A transition and/or change in parameter value may be, for example, a shift in the average value measured over time or a shift in the average value sampled along one or more body lumens, e.g. body lumens of the GI tract. Other changes in parameter values may indicate a transition point or event, e.g. a peak in the value of a parameter, etc and may be detected by transition detecting unit 15.

The confidence level that a transition from one region to another, e.g., a transition from the small intestine to the cecum occurred and/or that an event was identified may be determined (206). Confidence level may be determined by methods described herein and/or by methods known in the art and may be computed by transition detecting unit 15. The confidence level may be determined based on one or more parameters measured along the path traveled by in-vivo device 10, e.g. one or more pixel parameters, structure related parameters, other sensor output parameters. The confidence level that a transition or an event occurred may increase when more than one parameter is considered, for example, when more than one parameter indicates a shift in value in substantially the same location, point in time or in a predetermined distance from each other.

In one embodiment, a transition point, a specific location along the body lumen, and/or an event may be identified. In one example, the transition point may be identified when the confidence level that the transition occurred may be higher than a predetermined threshold. Other suitable methods may be used to check the reliability of an identified transition point, location and/or a correspondence between a shift and or change in one or more parameter values and a specific location in a body lumen. In one example, a transition point may be estimated as the average transition point from the transition points detected by the different parameters measured. In another example the transition point may be weighted average based on confidence level and based on a probability that each of the parameters may identify the transition correctly. In yet another example, the transition point that may be estimated as the transition point that yielded the highest confidence level. The confidence level that a specific location, e.g. a transition from one body lumen to another, in the GI was identified may increase when more than one parameter indicate a transition point in substantially the same location or in a predetermined distance from each other.

Transition points may be used to identify in-vivo regions within an image stream, e.g. esophagus, stomach, small intestine, colon. Other transition points, locations and/or events may be identified. Indication of a transition, for example, by segmentation of an image stream, may be shown on a display 16, such as a monitor. Transition points and/or identified regions may be indicated to a user, for example during or prior to display of the image stream. In one example, indication may be a graphical presentation as may be described in US Patent Application Publication Number 2005-0075551 published on Apr. 7, 2005 which is assigned to the common assignee of the present invention and which is hereby incorporated by reference in its entirety.

Segmentation of the image stream and other data captured by in-vivo device 10 may be performed (207), for example by segmentation unit 19 based on the transition points identified. For example, the image stream may be segmented to esophagus images, stomach images, small intestine images, and colorectal images. Other segmentations may be achieved and/or defined. Segmentation of the captured data may help decrease the time a health professional may require to review data, prepare a report and/or make a diagnosis. For example, a health professional may choose the segment of the image stream that is of interest to him and may only view images in that segment. This may save him time that would otherwise be spent on locating the segment of interest and reviewing segments of the movie that may be unrelated to the diagnosis or screening that may be required in a particular case.

According to other embodiments the method for detecting transition points may be implemented using data captured by other in-vivo devices having other suitable structures.

In some cases a passage or transition from one in-vivo location to another (for example, from one type of blood vessel to another or from one portion of the GI tract to another, e.g. stomach to small bowel or small bowel to large intestine) may be identified by a change in color or pixel value of the images, e.g., due to changes in tissue color or content, and/or by a change in scenery, e.g. a change in the structure, form or features of the tissue or content within the body lumen. Tissue pixel and/or color parameter (e.g., hue value) may be defined as an average color, for example over pixels that meet certain morphological, pattern, and/or color conditions. According to some embodiments one or more parameters of an image, for example, one or more colors, intensity, etc, may be selected and a transition point may be estimated for that parameter over a predefined region (e.g., data obtained from a predefined region). Other parameters may be used. Selecting/rejecting a transition point and/or determining the probability that a transition occurred may be based on a measure of confidence level. For example, formula I may be used to calculate confidence level that a transition point may have occurred.

$$M = \frac{|m_1 - m_2|}{s_1 + s_2} \qquad \text{Formula I}$$

Figure 3A:
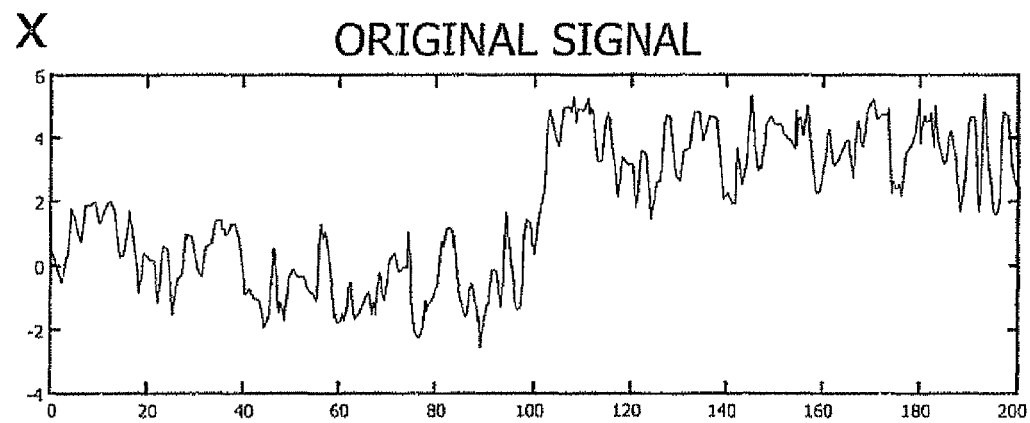
FIG. 3A depicts a graph which illustrates a parameter value 'X' over a stream of image frames according to an embodiment of the invention.
Figure 3B:
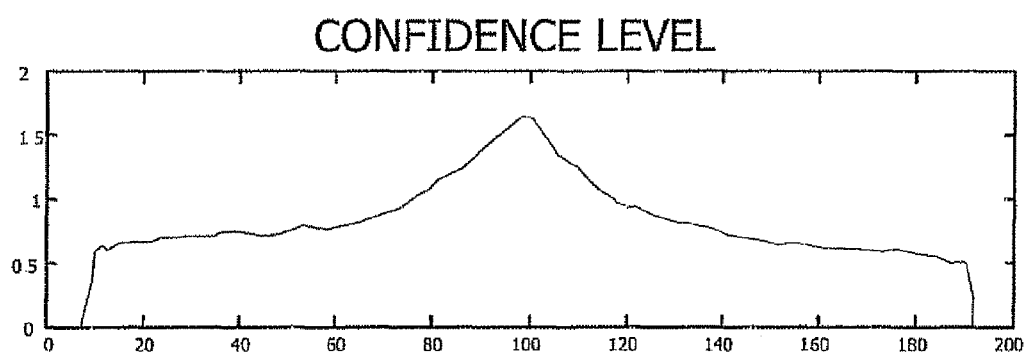
FIG. 3B depicts a graph which illustrates a confidence level of a transition based on parameter value 'X' over a stream of image frames according to an embodiment of the invention.

A confidence level (M) may be determined where $m_1$ is an average value of a parameter for a first group of image frames (and/or a parameter that corresponds to a first group of images); $m_2$ is an average value of a parameter for a second group of image frames; $S_1$ is a variance parameter (such as for example the standard deviation, the maximum deviation or other deviation measurements) for the first group of images and $S_2$ for the second group. A group of images may include two or more images from an in-vivo image stream. In other examples $m_1$ and $m_2$ may be average values for a single image. According to an embodiment of the invention it is expected that the confidence level M may be highest and/or may peak at the transition point, for example, if the parameter is average color, the peak may occur at a point where the average color of images (or image groups or sets) may be most different. In other embodiments $m_1$ and $m_2$ may be average values of parameters based on output from non-image sensors, e.g. temperature sensor, pH sensor, location sensor, etc. As such $m_1$ may be an average value of a parameter that was sampled at a time or location corresponding to the time or location that a first group of images were captured and $m_2$ may be an average value of a parameter that was sampled at a time or location corresponding to the time or location that a second group of images was captured. Sample graphs using this method, according to one embodiment, are illustrated, for example, in FIGS. 3A and 3B. As depicted in the graph in FIG. 3A, a parameter 'X' of an image stream (e.g., a color parameter) may on maintain a certain level for image groups 1-100 (depicted on the horizontal axis) and may on average maintain a different level for images groups 100-200. In one example, the confidence of level for changes in the parameter level 'X' may be shown in FIG. 3B. The confidence level pay peak, for example at or substantially around or near image group 100. An image group may include one or more image frames from an in-vivo image stream. In other examples, other suitable patterns of parameter and confidence levels may occur and may be used to detect transition points and or events.

In one example average tissue color may be used as a parameter to detect a transition point. The portion of gathered data that may be used to define average tissue color may be based one or more conditions and/or criteria. For example, conditions on the pixels that are taken for averaging may include Green/Red ratios lower than 0.7 and/or Blue/Green ratios higher than 0.65 and/or non-saturated regions (values in the .jpg image below 250 counts) and/or more than 100 pixels passing the conditions defined above and/or by using only pixels that are above the median value but no less than 100 counts. Other conditions may be used to define the data to be used to determine transition points and/or to define the data used to determine in-vivo location.

According to some embodiments spatial-spectral characteristics may be used to identify a transition point or a specified area and/or organ. For example, the surface of the stomach may be smoother than the surface of the small intestine, thus, stomach images may have less high frequency energy as compared to the small intestine. In the frequency domain there may be a clear separation between the two different groups of images in one and/or some of the frequency bands. According to some embodiments of the present invention, transition points may be identified in the frequency domain. Testing, for example, confidence level testing as may be described herein may be performed on portions of images, sub images or on whole images or sets of images.

Figures 4A, 4B:
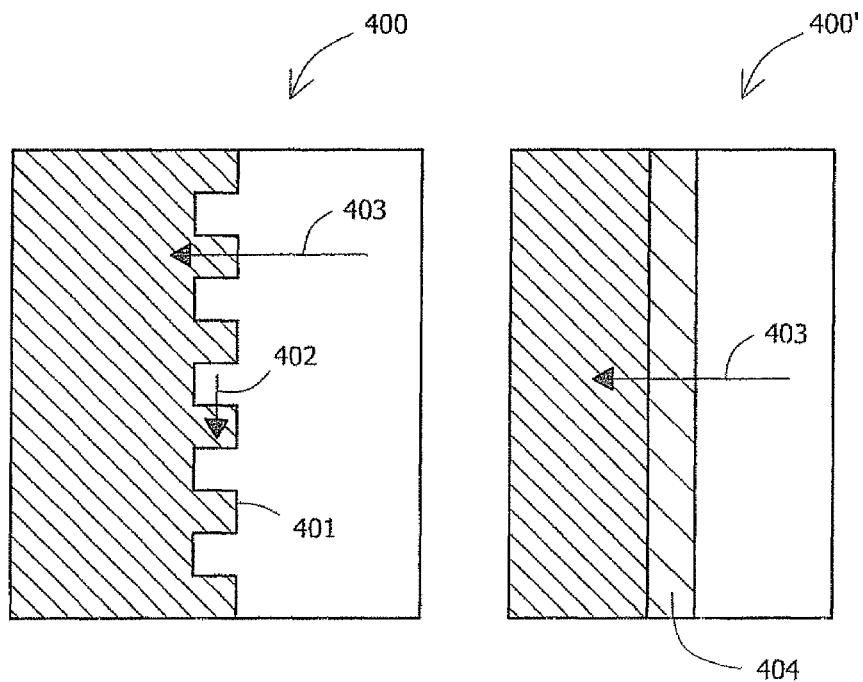
FIG. 4A is a schematic illustration of a sample villi structure according to an embodiment of the invention.
FIG. 4B is a schematic illustration of a sample villi structure at a low resolution according to an embodiment of the invention.

According to other embodiments of the invention shape parameters (for example, different anatomical structures) may be used to identify a transition point. One example of an anatomical structure (e.g., villi) is schematically illustrated in FIG. 4A. Villi are minute papillary processes visible on certain vascular membranes. For example, villi may cover the lining of the small intestines, but may not appear in other regions of the GI tract, e.g. may not appear in the stomach and large intestine. As illustrated in FIG. 4A villi structures 400 may be treated as edges having a characteristic tooth like structure 401. Considerations in identifying shapes and/or structure such as villi may include known image processing procedures, such as edge detection. In one example, villi may be identified by comparison of edges at high resolution and low resolution. An example of the villi structure at a low resolution 400' is illustrated in FIG. 4B. In one example, there may be a substantial difference between edge features and/or frequency content of an edge when examining an image frame at a high and a low resolution. For example, at a high resolution, an edge may be detected in the direction indicated by arrow 403 as well as in the direction indicated by arrow 402. In another example, at a low resolution the teeth structure 401 may be blurred and therefore an edge 404 may only be detected in the direction indicated by arrow 403. In one embodiment of the present invention, comparison of the edge detected in high and low resolution may be used to detect the presence of villi structures in one or more image frames.

Other methods may be used to detect the presence of villi structures, for example, methods based on color and structure identified in an image frame. In other embodiments edge line may have detectable high frequency content (or e.g. sharp curvature) that may be detectable in the frequency domain.

Figure 5:
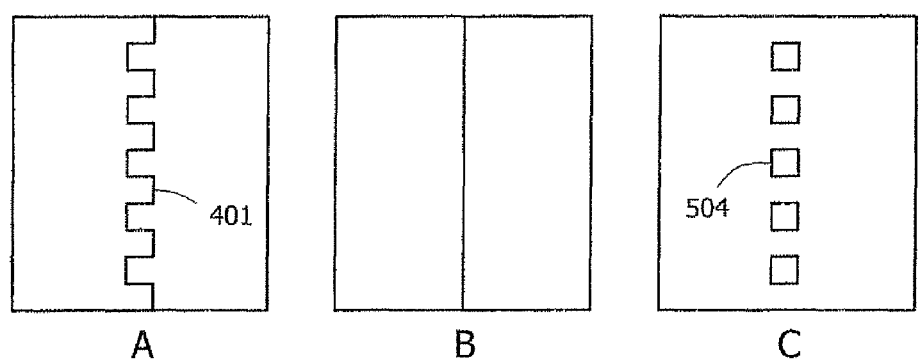
FIG. 5 is a schematic illustration of results that may be obtained when implementing morphologic operations to identify a villi structure according to an embodiment of the present invention.

Reference is now made to FIG. 5 a schematic illustration of results that may be obtained when implementing morphologic operations to identify a villi structure. According to some embodiments, known morphologic operations such as opening and/or closing may be applied on tissue segments to detect the presence of villi structures. According to one example, the form shown in A may be, for example, a segment of tissue with villi structures 401 as may be imaged by device 10. A closing operation may be performed yielding the structure in B. Subtraction of the villi structure A with the structure B may yield the forms 504 in C. Forms 504 may be detectable and may indicate the presence of villi structures.

According to some embodiments of the present invention, the absence of villi structures in the small intestine may be detectable and indicative of pathology, for example, Celiac. Detection of areas in the small intestine that may lack villi structures may enable diagnosis of pathology, e.g. Celiac. For example, one or more parameters may be used to identify the images frames from an image stream that may have been captured in the small intestine. Villi detection may then be implemented to screen for and/or diagnose Celiac.

According to some embodiments localization methods, for example, as described in embodiments of US Patent Application Publication Number 2002-0173718, filed on May 20, 2002, which is assigned to the common assignee of the present application and which is hereby incorporated by reference in its entirety may be used in combination with location and/or transition point determining methods to detect in-vivo location.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

The invention claimed is:

1. A method for segmenting an image stream captured within a gastrointestinal tract by an in vivo device inserted into said gastrointestinal tract, said device comprising an imager and being designed to pass through said gastrointestinal tract and to capture a stream of images thereof, the method comprising:
   receiving a first image and a second image of the image stream captured using said imager during a single pass of the device through the gastrointestinal tract, wherein the first image and the second image correspond to first and second chronological points in a time scale of the image stream, respectively;
   computing, using a computer, average pixel color values of the first image and of the second image;
   computing average tissue color based on RGB images with a predetermined number of pixels that pass at least one condition selected from: pixel ratio of red pixels to green pixels which passes a predetermined threshold, and pixel ratio of green pixels to blue pixels which passes a predetermined threshold;
   detecting, using a computer, a transition between organs of the gastrointestinal tract based on a change in the average pixel color values; and
   segmenting the image stream at the points in the time scale of the image stream that correspond to transitions between the organs of the gastrointestinal tract.

2. The method according to claim 1 wherein the organs of the gastrointestinal tract include the esophagus, stomach, small intestine, colon, rectum and the transverse colon.

3. The method according to claim 1 further comprising determining a confidence level of at least one of the transitions.

4. The method according to claim 1 wherein determining a confidence level comprises computing a deviation of the average pixel color values corresponding to a group of image frames from the image stream.

5. The method according to claim 1 further comprising computing intensity values of pixels in the first image and in the second image; and identifying a change in the intensity values between the first image and the second image.

6. The method according to claim 1 further comprising computing a speed or acceleration parameter to detect the movement pattern of the device through the gastrointestinal tract.

7. The method according to claim 1 further comprising displaying a segmented portion of the image stream.

8. The method according to claim 7 further comprising displaying a segmented image stream.

9. The method according to claim 1 comprising computing a location parameter to detect the movement pattern of the device through the gastrointestinal tract.

10. The method according to claim 1 further comprising identifying, using a computer, a change in the characteristics of a movement pattern of the device through the gastrointestinal tract to detect a transition through the transverse colon.

11. A system for segmenting an image stream captured within a gastrointestinal tract comprising:
    an in vivo device comprising an imager to capture the image stream from within the gastrointestinal tract during a single pass of said device through the gastrointestinal tract, wherein the image stream comprises a first image and a second image that correspond to first and second chronological points in a time scale of the image stream, respectively;
    a parameter computing unit to compute average pixel color values of the first image and the second image and to compute average tissue color based on RGB images with a predetermined number of pixels that pass at least one condition selected from: pixel ratio of red pixels to green pixels which passes a predetermined threshold, and pixel ratio of green pixels to blue pixels which passes a predetermined threshold;
    a transition detecting unit to detect a transition between organs of the gastrointestinal tract by identifying a change in the average pixel color values between the first image and the second image; and
    a segmentation unit to segment the image stream at the points in the time scale of the image stream that correspond to transitions between organs of the gastrointestinal tract.

12. The system according to claim 11 wherein the transition detecting unit indicates a point along the time scale that corresponds to the transition.

13. The system according to claim 11 wherein the transition detecting unit determines a confidence level of at least one of the transitions.

14. The system according to claim 13 wherein the transition detecting unit determines a confidence level based on a deviation of the average pixel color values corresponding to a group of image frames from the image stream.

15. The system according to claim 13 wherein the transition detecting unit further computes intensity values of pixels in the first image and the second image; and identifies a change in the intensity values between the first image and the second image.

16. The system according to claim 11 comprising a display unit, wherein the display unit displays at least a segment of the image stream.

17. The system according to claim 16 comprising a display unit, wherein the display unit displays a segmented image stream.

18. The system according to claim 11 wherein the transition detecting unit detects a transition through the transverse colon by identifying a change in the characteristics of a movement pattern of the device through the gastrointestinal tract.

19. The system according to claim 18 comprising a location sensor wherein the location sensor senses a location of the in-vivo device, wherein the transition detecting unit identifies the change in the characteristics of the movement pattern of the device based on the sensed location of the in-vivo device.

* * * * *